United States Patent

Aono et al.

[11] Patent Number: 5,823,775
[45] Date of Patent: Oct. 20, 1998

[54] PRACTICAL CUTTING BUR AND METHOD OF TRAINING USING SAME FOR THE CUTTING OF HUMAN TEETH

[75] Inventors: Masao Aono; Kohji Yamamoto, both of Gifu-ken; Kanji Matsutani; Satoshi Tezuka, both of Tochigi-ken, all of Japan

[73] Assignee: Kabushiki Kaisha Matsutani Seisakusho, Tochigi-ken, Japan

[21] Appl. No.: 568,387

[22] Filed: Dec. 6, 1995

[30] Foreign Application Priority Data

Dec. 9, 1994 [JP] Japan ................................... 6-306232

[51] Int. Cl.$^6$ ........................................................ A61C 3/02
[52] U.S. Cl. ............................................. 433/166; 434/263
[58] Field of Search .................................... 433/125, 142, 433/165, 166, 215; 434/263

[56] References Cited

U.S. PATENT DOCUMENTS

| | | | |
|---|---|---|---|
| 959,054 | 5/1910 | Glover | 433/166 |
| 2,562,587 | 7/1951 | Swearingen | 433/166 |
| 3,309,772 | 3/1967 | Lieb et al. | 433/166 |
| 4,684,346 | 8/1987 | Martin | 433/166 |
| 4,897,037 | 1/1990 | Appleby | 433/166 |

FOREIGN PATENT DOCUMENTS

| | | | |
|---|---|---|---|
| 2464697 | 4/1981 | France | 433/166 |
| 6022982 | 2/1994 | Japan | 433/166 |

*Primary Examiner*—Ralph A. Lewis
*Attorney, Agent, or Firm*—Townsend & Banta

[57] ABSTRACT

Diamond bur A has base metal 1 formed with cylindrical shank 1b on one side of diamond bur A, and cutting portion 1a formed on base metal 1 on the other side of diamond bur A extending over a given length from an end of diamond A. A mixture 2 of various abrasive grains with three different grain sizes are secured to cutting portion 1a. Since various abrasive grains with different grain sizes are secured to cutting portion 1a, with the increase of load applied on artificial tooth, the number of abrasive grains contributing to cutting increases, and the machinability is improved. This tendency is equal to the machinability of the diamond bur on the market for cutting human dentin, or dental enamel.

3 Claims, 3 Drawing Sheets

PRACTICAL CUTTING BUR AND METHOD OF TRAINING USING SAME FOR THE CUTTING OF HUMAN TEETH

BACKGROUND OF THE INVENTION

1. Field of the Invention

The present invention relates in general to a cutting bur and method of training to use same for the cutting of human tooth, and, more particularly, to a practice cutting bur which enables students of dentistry to grasp the same sense of cutting a human tooth by cutting an artificial tooth using the cutting bur of the present invention.

2. Description of the Prior Art

Conventional dental treatment is carried out with a diamond bur provided with a cutting portion having abrasive grains of uniform grain sizes secured on a base metal and the bur is attached to an air motor. As an example, a diamond bur is used which is rotated by the air motor. As the diamond bur is pressed against human dentin or dental enamel, a cavity or an abutment is formed. For this reason, students of dentistry need training in the cutting of a human tooth with a diamond bur.

It is preferable to have the above-mentioned training using human teeth. However, it is difficult to collect a sufficient number of human teeth for this purpose because extractions of teeth have decreased by reason of the development of improved dental treatment. Therefore, artificial teeth made of epoxy resin or polypropylene resin are provided for the practical training of dentists.

However, a problem arises because the time required for the machinability of the artificial tooth cut by a diamond bur differs from the time of machinability of human dentin or dental enamel cut by a diamond bur to the same depth and under the same applied load. Consequently, under the same condition of operation of an air motor, if the tooth materials to be cut changes the cutting depth of a cavity to be formed changes.

During a dental treatment, it is practically impossible to operate an air motor and measure the pressure of the diamond bur against a human tooth when cutting human dentin or dental enamel. Therefore, the difference between the sense of cutting with a diamond bur which students of dentistry experience in training, will differ from the sense of cutting with diamond bur in cutting human teeth in a dental treatment. Therefore, this makes training in cutting teeth with a diamond bur somewhat worthless. For this reason, it is desirable to develop a method of having practical training in cutting human teeth to enable students of dentistry to experience the sense of cutting with a diamond bur in dental treatment.

BRIEF SUMMARY OF INVENTION

It is an object of the present invention to provide a practical cutting bur which enables students of dentistry to experience the same sense of cutting by using an artificial plastic tooth as they will in cutting a human tooth with a diamond bur during a dental treatment.

A second object of the present invention is to provide a method of practical training for dentistry students in the cutting of human teeth by cutting artificial teeth made of plastic using a cutting bur attached to a rotary instrument in which students of dentistry can experience the same sense of cutting a human tooth with a diamond bur.

The first object of the present invention is achieved, according to the present invention, by an improved cutting bur comprising a cutting portion formed on a base metal, the cutting portion having a mixture of various abrasive grains with different grain sizes secured to the cutting portion.

Further, the first object of the present invention is achieved, according to the present invention, by a practical cutting bur comprising a shank which has an end held by a rotary instrument, and a cutting portion which is an integral part of the shank, the surface of the cutting surface having a mixture of various abrasive grains of different grain sizes secured to the cutting portion.

In the above-mentioned cutting bur of the present invention, the cutting portion tapers toward the top thereof.

In the above-mentioned cutting bur of the present invention, the mixture of various abrasive grains having different grain sizes is composed of abrasive grains having a grain size number #600, abrasive grains having a grain size number #230, and abrasive grains having grain size number #120.

Further, according to the present invention, the mixture of abrasive grains can contain 25% of abrasive grains of grain size number #600, 50% of abrasive grains of grain size number #230, and 25% of abrasive grains of grain size number #120. In a preferred embodiment, the abrasive grains comprise a mixture of 50% of abrasive grains of grain size number #600, 25% of abrasive grains of grain size number #230, and 25% of abrasive grains of grain size number #120. In another preferred embodiment the abrasive grains comprise a mixture of 25% of abrasive grains of grain size number #600, 25% of abrasive grains of grain size number #230, and 50% of abrasive grains of grain size number #120.

The second object of the present invention is achieved, according to the present invention, by a method of practical training in the cutting of human teeth by cutting artificial tooth made of plastic such as epoxy or polypropylene using the cutting bur of the present invention attached to a rotary instrument, wherein the cutting bur comprises a shank having an end held by the rotary instrument, and a cutting portion which is an integral part of the shank, the cutting surface of the bur having a mixture of various abrasive grains with different grain sizes secured to the cutting portion.

In the above-mentioned method, the cutting bur of the present invention can be used, having on its cutting surface a mixture of various abrasive grains with different grain sizes, composed of abrasive grains of grain size number #600, abrasive grains of grain size number #230, and abrasive grains of grain size number #120.

Further, in the above-mentioned method, the cutting bur of the present invention can be used, which has on its cutting surface any one of a mixture of 25% of abrasive grains of grain size number #600, 50% of abrasive grains of grain size number #230, and 25% of abrasive grains of grain size number #120, a mixture of 50% of abrasive grains of grain size number #600, 25% of adhesive grains of grain size #230, and 25% of adhesive grains of grain size #120, or a mixture of 25% of adhesive grains of grain size #600, 25% of adhesive grains of grain size #230, and 50% of adhesive grains of grain size #120.

When using the cutting bur of the present invention, the sense of cutting an artificial tooth made of plastics such as epoxy resin or polypropylene is nearly equal to the sense of cutting a human tooth with diamond bur.

DETAILED DESCRIPTION

Figure 1:
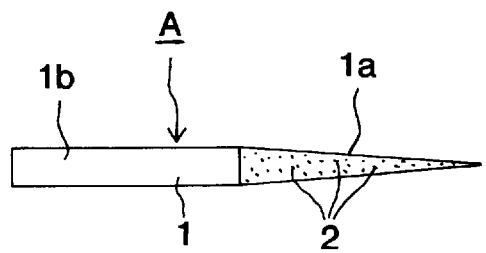
FIG. 1 is a side view showing the construction of the bur of the present invention.
Figure 2:
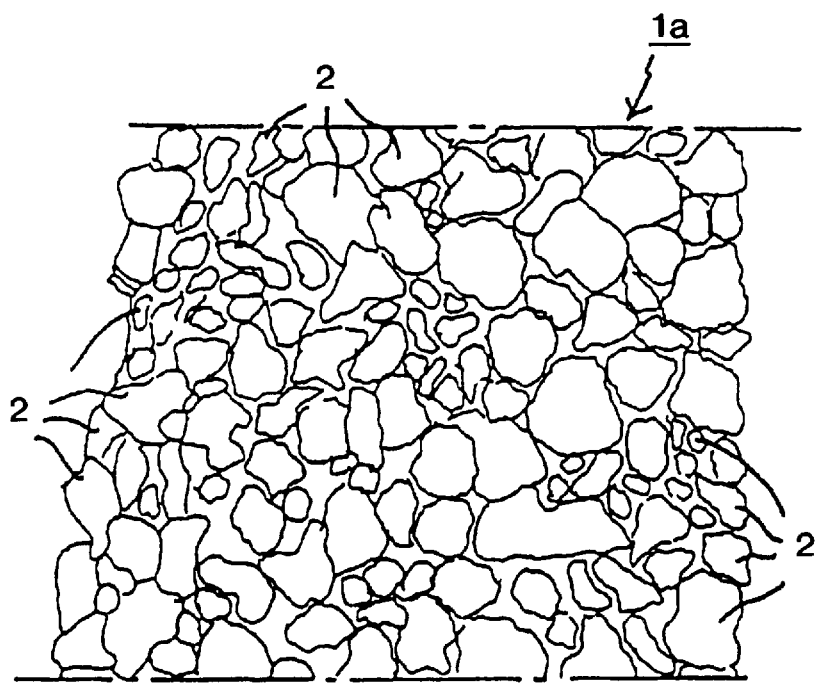
FIG. 2 is an enlarged view of the cutting portion of the bur of the present invention, illustrating the various sized abrasive grains on the surface thereof.

Referring to FIGS. 1 and 2, the construction of diamond bur A of the present invention is illustrated. The diamond bur of the present invention is provided with abrasive grains secured to a base metal although the use of a bur is a "grinding technique". The term "cutting" is used herein since this term is used in dentistry and by the Japanese Welfare Ministry.

Referring to FIGS. 1 and 2, diamond bur A of the present invention comprises stick-shaped base metal 1 formed with cylindrical shank 1b on one end and a cutting portion 1a formed on base metal 1 on the other end-and extending over a given length from an end of diamond bur A. Shank 1b is held by a chuck of an air motor (not shown). The number of revolutions of an air motor is desirably from $16\times10^4$ r.p.m. to $45\times10^4$ r.p.m. when a tooth is cut by diamond bur A.

As shown in FIG. 2, a mixture 2 of abrasive grains made of either diamond, cubic system boron nitride or the like is used having grain size number #600, #230, and #120, respectively mixed in an appropriate ratio determined according to material from which an artificial tooth is formed. The abrasive grains are secured to base metal 1 in cutting portion 1a. In one example, an artificial tooth made of epoxy resin is cut with diamond bur A, having on its cutting surface a mixture of 25% of abrasive grains of grain size number #600, 50% of abrasive grains with grain size number #230, and 25% of abrasive grains with grain size number #120.

The size of abrasive grain represented by grain size number is as shown in the following Table 1.

TABLE 1

| Grain size number | Grain size of diamond used | Reference in average grain size in micron |
| --- | --- | --- |
| #120 | 120~140 | 125 |
| #230 | 230~270 | 63 |
| #600 | 20~30 | 25 |

In order to secure a mixture of grains to base metal 1, as disclosed in Japanese Patent Publication (Kokai) Heisei 1(1987)-140157, base metal 1 and a container containing a mixture of abrasive grains are dipped into an electrolyte in which a metal, such as nickel, is dissolved. In this way a metallic layer can be formed on base metal 1 by electroplating, while the mixture of abrasive grains can be secured in the metallic layer. In the diamond bur A, FIG. 1, abrasive grains having various grain sizes can be secured to base metal 1 using this process.

In the conventional diamond burs, abrasive grains having equal grain sizes selected according to the purpose of cutting of an artificial tooth are secured to base metal 1. Using the diamond bur, a cavity of the desired shape can be formed by cutting human dentin, and dental enamel with the nearly same sense of cutting by diamond bur.

In diamond bur A of the present invention in which mixture A of abrasive grains composed of grains having various grain sizes is secured to base metal 1, abrasive grains having larger grain sizes and abrasive grains having smaller grain sizes are wholly put on base metal 1. As a result, a large number of pockets for letting cutting dusts off are formed between abrasive grains having various grain sizes.

First, since an artificial tooth is softer than a human tooth and has larger elasticity than a human tooth, the entering length of cutting portion 1a into an artificial tooth changes according to the force applied on diamond bur A. Namely, when the load is smaller, an artificial tooth is cut by parts of abrasive grains projecting out in cutting portion 1a (abrasive grains having relatively larger abrasive grain sizes), and as loads are increased, the whole abrasive grains secured to base metal 1 in cutting portion 1a will be used for cutting of artificial tooth. Then, cutting dusts of an artificial tooth generated by cutting the artificial tooth with diamond bur A are removed through pockets formed between abrasive grains. Namely, when an artificial tooth is cut by diamond bur A of the present invention, with the increase of load, the machinability of diamond bur A can be increased.

A man, which has practical training in cutting human teeth, can grasp the same sense of cutting an artificial tooth with a diamond bur as that which is experienced when a human tooth is cut by diamond bur having the above-mentioned machinability.

Then, the machinability of cutting an artificial tooth made of epoxy resin by diamond bur A of the present invention is comparable with the machinability of cutting a human tooth with a conventional diamond bur on the market. When comparing both of these machinabilities, an experimental equipment as shown in FIG. 3 is used, in which the cutting depth of material to be cut is measured against applied load.

Figure 3:
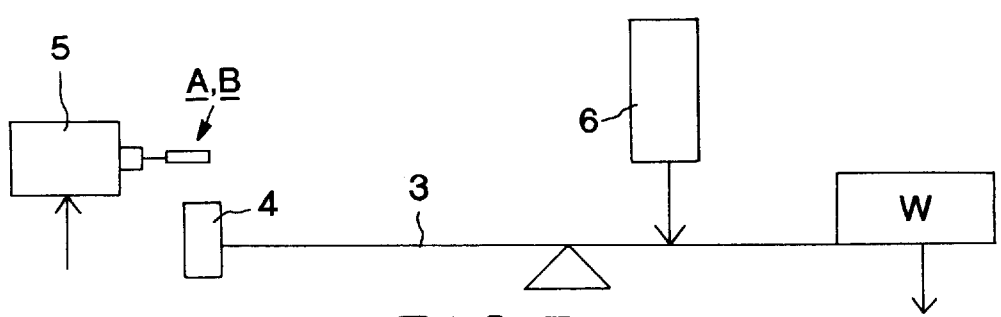
FIG. 3 is a schematic representation showing experimental equipment for measuring the machinability of the bur of FIG. 1.

The construction of an experimental equipment shown in FIG. 3 is explained as follows. The experimental equipment has pendulum 3, one end of which is provided with weight W, and to the other end of which material 4 to be cut such as an artificial tooth made of epoxy resin or human tooth is attached. Air motor 5 is fixed opposite to material 4 to be cut, and diamond bur A of the present invention or diamond bur B on the market is held by air motor 5. Sensor 6 for measuring an amount of displacement of pendulum 3 is disposed on a given place on pendulum 3, by which the cutting depth of material to be cut per hour can be measured under the state where a given load is applied to either diamond bur A or diamond bur B.

Figure 4:
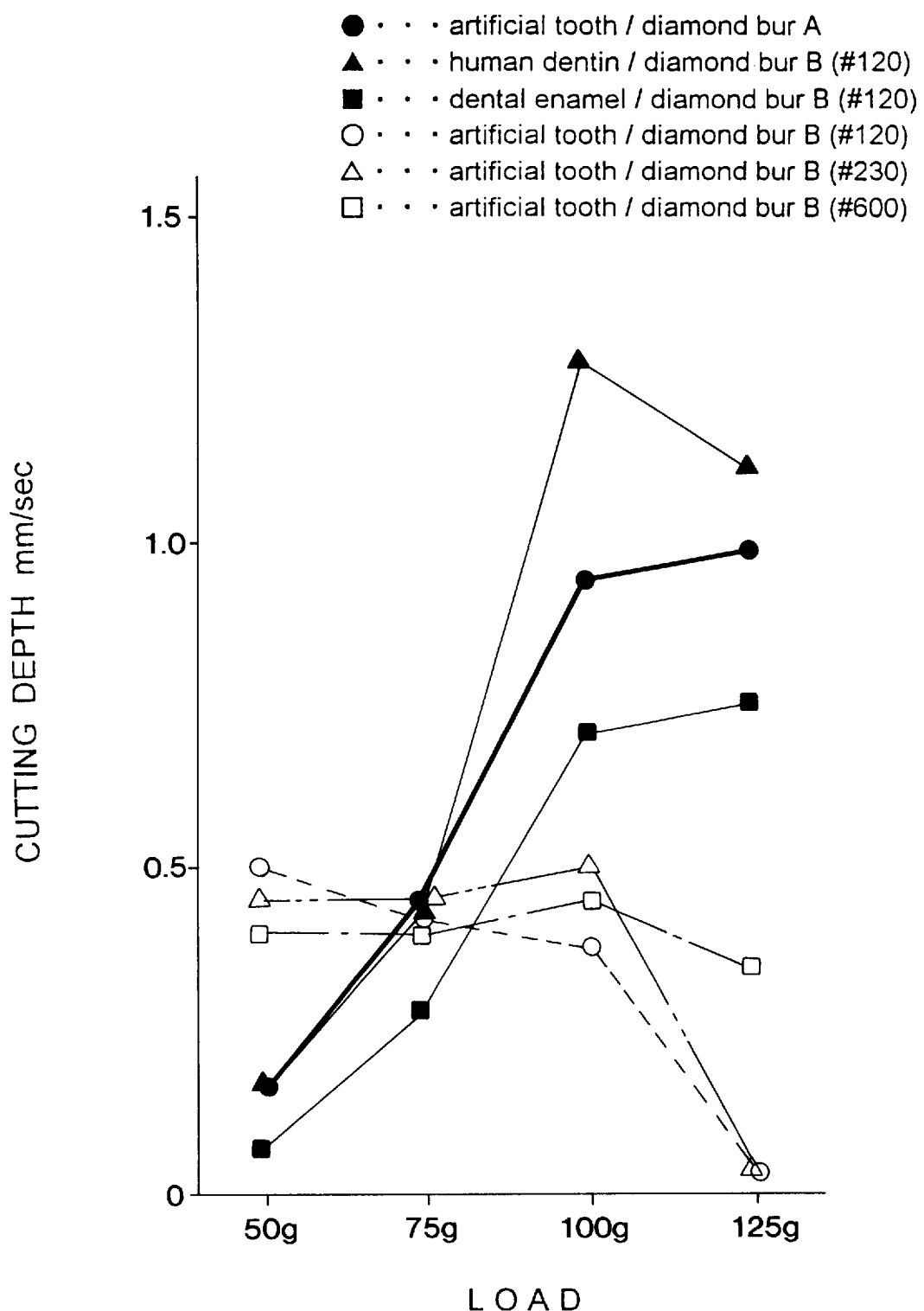
FIG. 4 is a graphical representation comparing the machinability of the bur of the present invention when cutting an artificial tooth made of epoxy resin with the machinability of a conventional diamond bur when cutting human dentin and dental enamel.

Diamond bur A of the present invention, and diamond bur B on the market are held by an air motor 5 in the above-mentioned experimental equipment, and samples of an artificial tooth made of epoxy resin, and human dentin and dental enamel as material to be cut are attached to one end of pendulum 3. The cutting depths per hour when loads W is 50 g, 75 g, 100 g, or 125 g is measured. The results are shown in FIG. 4. In the experiment, an air motor with numbers of revolutions of $20 \times 10^4 \sim 30 \times 10^4$ r.p.m. is used.

In FIG. 4, plot —●— indicates cutting depth mm/sec against load g of the time when an artificial tooth made of epoxy resin is cut by diamond bur A, plot —▲— indicates cutting depth mm/sec against load g of the time when human dentin is cut by the diamond bur B on the market having abrasive grains of grain size number #120, and —■— indicates cutting depth mm/sec against load g of the time when dental enamel is cut by the diamond bur B on the market having abrasive grains of grain size number #120. Further, plot —□— indicates cutting depth mm/sec against load g of the time when an artificial tooth made of epoxy resin is cut by diamond bur B on the market having abrasive grains of grain size number #600, plot —△— indicates cutting depth mm/sec against load g of the time when an artificial tooth made of epoxy resin is cut by diamond bur B having abrasive grains of grain size number #230, and plot —○— indicates cutting depth mm/sec against load g of the time when an artificial tooth made of epoxy resin is cut by the diamond bur B on the market having abrasive grains of grain size number #120.

As is apparent from FIG. 4, when an artificial tooth made of epoxy resin is cut by diamond bur A of the present invention, though the machinability changes according to grain size of abrasive grains more or less, with the increase of load applied on diamond bur B, the machinability decreases. On the other hand, when dentin of human teeth or dental enamel is cut, with the increase of load, the machinability increases.

Since diamond bur B on the market has abrasive grains of uniform grain size, and the cutting portion thereof has the surface of a few quantity of unevenness, pockets formed between abrasive grains are uniform. When an artificial tooth with elasticity is cut, with the increase of load, entering depth of cutting portion 1a into the elastic artificial tooth increases, by which cutting dust which has entered into pockets formed between abrasive grains is hindered from being removed. As a consequence, as the load is increased, the machinability decreases. However, when human dentin or dental enamel is cut by diamond bur B, since they do not have the elasticity, with the increase of loads, the machinability increases since cutting dust is favorably removed through pockets formed between abrasive grains.

Further, when artificial teeth made of epoxy resin is cut with diamond bur A under the condition of the same load as that in diamond bur B, with the increase of load, the machinability increases. Though the numerical values of cutting depth against the respective loads differ with a case where artificial tooth made of epoxy resin is cut by diamond bur A of the present invention, and a case where human dentin or dental enamel is cut by diamond bur B, the data shows that the tendency of the machinability to increase is the same as when human dentin or dental enamel is cut by diamond bur B.

As mentioned herein above, a tendency of the time when artificial teeth made of epoxy resin is cut by diamond bur A of the present invention is nearly the same as a tendency of the time when dentin of human teeth or dental enamel is cut by diamond bur B on the market. Accordingly, a sense of operation of the time when human dentin or dental enamel is cut by diamond bur B on the market can be experienced by becoming skilled in an operation of the time when an artificial tooth made of epoxy resin is cut by diamond bur A of the present invention.

In the above-mentioned example, a mixture of 25% of abrasive grains of grain size number #600, 50% of abrasive grains of grain size number #230, and 25% of abrasive grains of grain size number #120 (as shown in ① in Table 2) is used. However, as shown in ② in Table 2, a mixture of 50% of abrasive grains of grain size number #600, 25% of abrasive grains of grain size number #230, 25% of abrasive grains of grain size number #120 (② in Table 2, or a mixture of 25% of abrasive grains of grain size number #600, 25% of abrasive grains of grain size number #230, and 50% of abrasive grains of grain size number #120 (③ in Table 2) can be used.

TABLE 2

| No. | #600 | #230 | #120 |
|-----|------|------|------|
|     | 25%  | 50%  | 25%  |
|     | 50%  | 25%  | 25%  |
|     | 25%  | 25%  | 50%  |

Further, the present example is explained about a case where an artificial tooth made of epoxy resin is cut by diamond bur A of the present invention. However, it is not always necessary that an artificial tooth is made of epoxy resin. An artificial tooth may be made of polypropylene resin and other types of resins. Further, there is a case where the stickiness and hardness of artificial tooth change according to material and filling material of an artificial tooth. Therefore, the grain size of abrasive grains and the mixture ratio should not be restricted to a given value. It is necessary that they are set suitably according to the material, and the stickiness and hardness of artificial tooth.

Figure 5A:
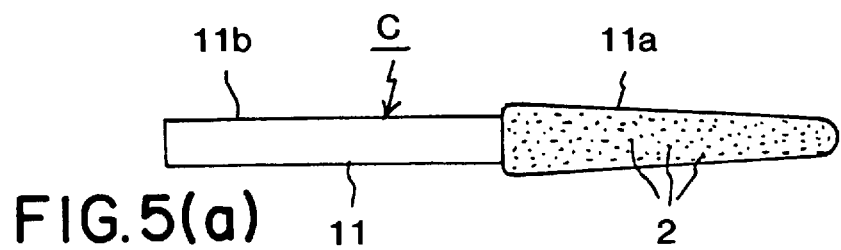
FIG. 5(a) shows an elongated shape of the bur of the present invention.
Figure 5B:
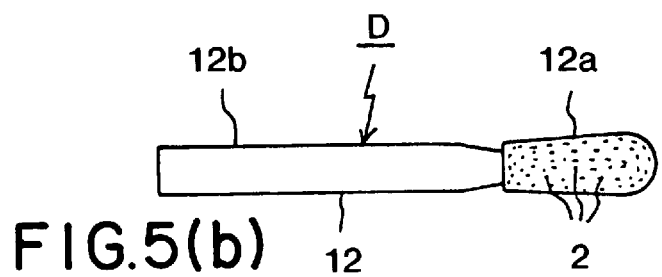
FIG. 5(b) shows another shape of the bur of the present invention.
Figure 5C:
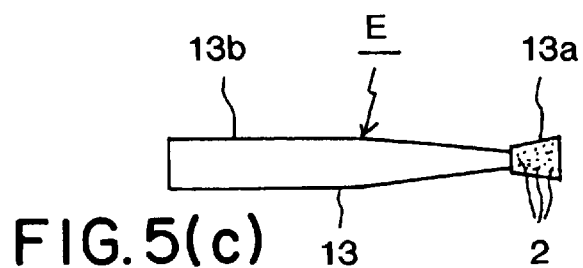
FIG. 5(c) shows a flat headed shape of the bur of the present invention.
Figure 5D:
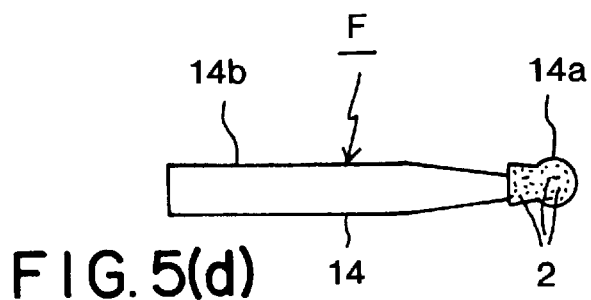
FIG. 5(d) shows a bur of the present invention with a rounded head.
Figure 5E:
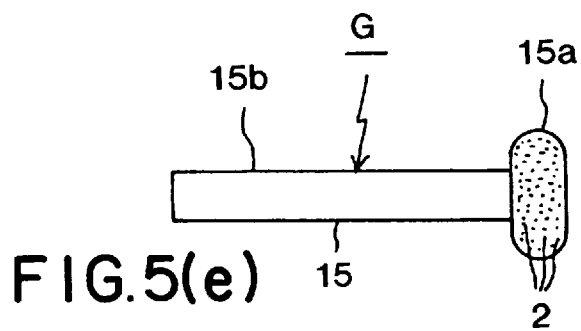
FIG. 5(e) shows still another shape of the bur of the present invention.

Further, the shape of diamond bur A of the present invention is not restricted to that shown in FIG. 1. As shown in FIG. 5(a) to (e), various shapes can be selected for the diamond bur of the present invention, wherein diamond bur C shown in FIG. 5(a) is provided with tapered-round-end-shaped cutting portion 11aformed on a portion of base metal 11, diamond bur D shown in FIG. 5(b) is provided with pestle-shaped cutting portion 12a formed on a portion of base metal 12, diamond bur E shown in FIG. 5(c) is provided with inverted-cone-shaped cutting portion 13a formed on a portion of base metal 13, diamond bur F shown in FIG. 5(d) is provided with ball-shaped cutting portion 14a formed on a portion of base metal 14, diamond bur G shown in FIG. 5(e) is provided with wheel-round-edge-shaped cutting portion 15a formed on a portion of base metal 15. Further, base metals 11, 12, 13, 14 and 15 are formed with cylindrical shanks 11b, 12b, 13b, 14b and 15b on the other hand which are held by an air motor in the same manner as in the above-mentioned first example.

As mentioned in detail hereinabove, a diamond bur of the present invention has various abrasive grains of different grain size. Therefore, it is possible that the time of machinability of artificial tooth made of epoxy resin, polypropylene resin or the like cut by a diamond bur of the present invention is nearly equal to the time of machinability of human dentin or dental enamel is cut by a diamond bur on the market. Therefore, even in a case where students of dentistry have training in the cutting of teeth with a diamond bur of the present invention, they can grasp the same sense of operation when a cavity is formed, or an abutment is formed for the treatment of tooth.

What is claimed is:

1. A method of practice training for the cutting of human teeth by cutting artificial teeth made of plastic by means of a practice cutting bur attached to a rotary instrument, wherein the practice cutting bur comprises a shank having one end adapted to be held by a rotary instrument, and another end of the shank having a cutting portion, said cutting portion having a surface, said cutting portion formed integral with said shank, and said cutting portion having, secured to the surface, a mixture of 25% of abrasive grains of grain size #600, 50% of abrasive grains of grain size #230, and 25% of abrasive grains of grain size #120.

2. A method of practice training for the cutting of human teeth by cutting artificial teeth made of plastic by means of a practice cutting bur attached to a rotary instrument, said practice cutting bur comprising a shank having one end adapted to be held by a rotary instrument, and another end of said shank having a cutting portion, said cutting portion having a surface, said cutting portion formed integral with said shank, and said cutting portion having, secured to the surface, a mixture of 50% of abrasive grains of grain size number #600, 25% of abrasive grains of grain size number #230, and 25% of abrasive grains of grain size number #120.

3. A method of practice training for the cutting of human teeth by cutting artificial teeth made of elastic by means of a practice cutting bur attached to a rotary instrument, said practice cutting bur comprising a shank having one end adapted to be held by a rotary instrument, and another end of said shank having a cutting portion, said cutting portion having a surface, said cutting portion formed integral with said shank, and said cutting portion having, secured to the surface, a mixture of 25% of abrasive grains of grain size number #600, 25% of abrasive grains of grain size number #230, and 50% of abrasive grains of grain size number #120.

* * * * *